United States Patent
Chin et al.

(10) Patent No.: US 9,125,638 B2
(45) Date of Patent: Sep. 8, 2015

(54) FLEXIBLE BIOPSY COLLECTION DEVICE AND RELATED METHODS OF USE

(75) Inventors: Yem Chin, Burlington, MA (US); Robert DeVries, Northborough, MA (US); Paul Scopton, Winchester, MA (US); John Hutchins, North Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2380 days.

(21) Appl. No.: 11/179,640

(22) Filed: Jul. 13, 2005

(65) Prior Publication Data

US 2007/0016099 A1      Jan. 18, 2007

(51) Int. Cl.
*A61B 10/02* (2006.01)
*A61B 17/29* (2006.01)

(52) U.S. Cl.
CPC ......... *A61B 10/0275* (2013.01); *A61B 10/0283* (2013.01); *A61B 2010/0225* (2013.01); *A61B 2017/2905* (2013.01)

(58) Field of Classification Search
CPC .................................................. A61B 10/0275
USPC .......... 600/565, 564, 566, 567, 585; 606/167, 606/170
See application file for complete search history.

(56) References Cited

U.S. PATENT DOCUMENTS

| | | | | |
|---|---|---|---|---|
| 5,106,364 A | * | 4/1992 | Hayafuji et al. | 604/22 |
| 5,527,331 A | * | 6/1996 | Kresch et al. | 606/170 |
| 5,562,102 A | * | 10/1996 | Taylor | 600/564 |
| 5,730,752 A | * | 3/1998 | Alden et al. | 606/180 |
| 5,762,069 A | * | 6/1998 | Kelleher et al. | 600/564 |
| 5,922,003 A | * | 7/1999 | Anctil et al. | 606/170 |
| 6,063,037 A | * | 5/2000 | Mittermeier et al. | 600/567 |
| 6,086,543 A | * | 7/2000 | Anderson et al. | 600/567 |
| RE38,335 E | * | 11/2003 | Aust et al. | 606/170 |
| 6,860,868 B1 | * | 3/2005 | Sussman et al. | 604/27 |
| 7,244,263 B2 | * | 7/2007 | Robison et al. | 606/170 |
| 7,296,577 B2 | * | 11/2007 | Lashinski et al. | 128/898 |
| 2002/0007190 A1 | * | 1/2002 | Wulfman et al. | 606/167 |

FOREIGN PATENT DOCUMENTS

WO   WO 02/062229      *   8/2002   ............ A61B 10/00
WO   WO 02/062229 A2      8/2002

* cited by examiner

*Primary Examiner* — Brian Szmal
(74) *Attorney, Agent, or Firm* — Bookoff McAndrews, PLLC

(57) ABSTRACT

Embodiments of the invention are directed to a medical device and methods for collecting a tissue sample from a patient's body. The device may include a first tube defining a lumen and an aperture at a distal end of the first tube. A second tube extends within the lumen of the first tube and defines a lumen and slots, where at least some of the slots have sharp edges configured to shear tissue. The second tube is movable relative to the first tube such that the sharp edges cut a plurality of samples from tissue disposed within the aperture.

76 Claims, 4 Drawing Sheets

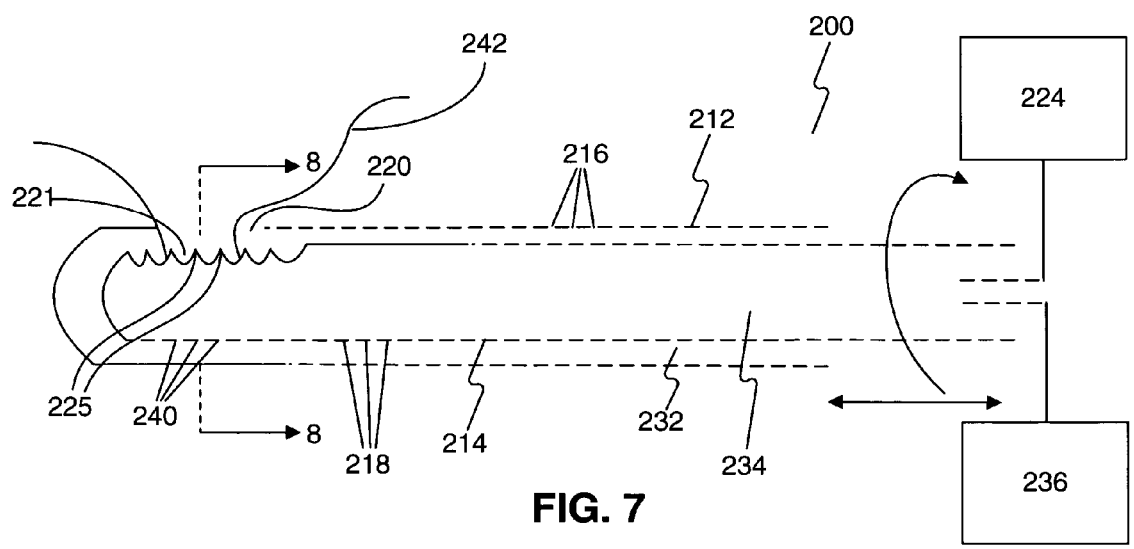
FIG. 7
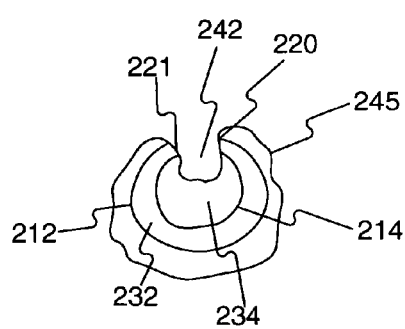 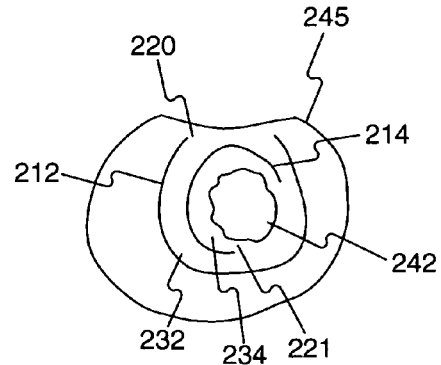
FIG. 8A  FIG. 8B

FLEXIBLE BIOPSY COLLECTION DEVICE AND RELATED METHODS OF USE

DESCRIPTION OF THE INVENTION

1. Field of the Invention

Embodiments of this invention relate to a flexible biopsy collection device and its related methods of use. More particularly, at least certain embodiments of the invention relate to a flexible, low profile, biopsy collection device for passage through a small diameter working channel of an endoscope and capable of collecting tissue samples adequate for pathology study.

2. Background of the Invention

A biopsy entails the surgical removal of tissue or cells from the body of a patient for pathological examination of the collected sample. The purpose for taking a biopsy sample is often to look for cellular shape changes represented in the collected sample. The identification of particular cellular shape changes in a collected specimen can be instrumental in the identification of cancer in a patient.

Endoscopes are often used to access and visualize a patient's anatomical lumen during a medical procedure. Once the endoscope is positioned in the desired body portion, a biopsy instrument can be advanced through the working channel of the endoscope to the desired body portion. The endoscopic and biopsy instruments may then be manipulated as desired for visualization and specimen sampling respectively.

Smaller diameter endoscopes are presently available in the endoscopy market that help reduce unnecessary trauma to the tissues of a patient and provide more versatile endoscopes capable of accessing more diverse categories of patient body lumens. Smaller diameter endoscopes often have smaller working channels, which limit the size of any auxiliary instrument used. This, in turn, limits the size, and often the quality of, any biopsy specimen collected.

Presently, several biopsy techniques (e.g., pinch biopsy, needle biopsy, and cytology brush) are used to obtain a biopsy specimen.

In general, a pinch biopsy is performed by a biopsy instrument having forceps with two jaws activated by an internal manipulating wire or wires. The instrument is passed through an endoscope to a desired location, and then the jaws are opened and closed to grab and sever the biopsy sample. The instrument with the detached sample is then withdrawn from the endoscope so that the sample is removed. If another biopsy specimen is needed, the forceps is then re-inserted into the endoscope and relocated for the next biopsy. Frequently, due to a small moment arm of the instrument, the cutting force of the jaws is not sufficient or the jaws are not sharp enough to cleanly shear the tissue which is then torn off by a pulling movement. In addition, such biopsy instruments may be too large for smaller diameter endoscopes with smaller diameter working channels.

A needle biopsy is usually performed with a two part device. The first part includes a stylet-needle shaft having a tissue retaining recess formed in a lateral side of the area close to the needle tip. When the needle is inserted into tissue from which a sample is desired, a portion of tissue extends into the recess. The second part typically includes an outer sheath, or cannula, that is fitted over the needle shaft and includes a blade formed at a distal end to cut off and encapsulate the tissue retained in the needle shaft recess. Such needle biopsy devices often cannot be positioned in flexible small diameter positioning devices because the puncturing stylet-needle is rigid.

To collect cells for cytological examination, a distal brush device is passed through an endoscope to a collection site. The brush is extended from its sheath and, by brushing the tissue, the cells are scraped and collected onto the bristles. The brush is retracted into the sheath to prevent decontamination, the instrument is withdrawn from the body, and the cells are deposited on glass slides for review. However, the brush can collect only tissue cells, which is often not sufficient since tissue samples are required for many histopathological evaluations.

In many situations, it is desirable to collect multiple biopsy specimens from the same location or several precisely defined locations. For example, when examining the spread of the diseased tissue, multiple biopsies are taken from several sites spread apart. In this process, if a biopsy instrument capable of collecting only a single specimen is used, the instrument must be withdrawn from the patient to remove the collected biopsy specimen before the next specimen can be taken. This substantially lengthens the biopsy process. For a subsequent biopsy, the physician has to re-insert and re-orient the biopsy instrument in relation to the subsequent biopsy site. The re-orientation may be quite difficult and time consuming since the biopsy instruments are often 200 cm long. The time delay may cause a fatigue of the medical team, requires a longer sedation time of the patient, and could also negatively affect the number and quality of the specimens which, in turn, could negatively influence the diagnosis.

Thus, it is desirable to have an alternative flexible, low profile biopsy device that can access small working channels of smaller endoscopic devices and obtain multiple large tissue samples adequate for pathology study.

SUMMARY OF THE INVENTION

Embodiments of the present invention are directed to medical devices for collecting biopsy samples within a patient's body that obviate one or more of the limitations and disadvantages of prior biopsy collection devices.

In one embodiment, the medical device includes a first tube defining a lumen and an aperture at a distal end of the first tube. A second tube extends within the lumen of the first tube, the second tube defining a lumen and slots, and at least some of the slots having sharp edges configured to shear tissue. The second tube is movable relative to the first tube such that the sharp edges cut a plurality of samples from tissue disposed within the aperture.

In various embodiments, the medical device may include one or more of the following additional features: a drive connected to the second tube configured to provide movement of the second tube relative to the first tube; wherein the drive moves the second tube relative to the first tube with simultaneous rotary and axial movement; wherein the second tube moves axially relative to the first tube; wherein the aperture is defined by a side surface of the first tube; wherein the first tube defines multiple apertures along a side surface of the first tube; wherein the sharp edges are arranged to cut the plurality of samples substantially simultaneously; wherein the slots extend transverse to a longitudinal axis of the second tube; wherein the slots extend only partially through a wall forming the second tube; wherein at least a portion of slots extend in a spiral pattern along the second tube; wherein at least one of the first and second tube is electrically conductive and configured to act as an electrode for conducting current to tissue; wherein the first tube defines slots along a portion thereof; wherein a proximal end of the second tube is connected to a vacuum source that provides suction within the lumen of the second tube; wherein a portion of an inside surface of the second tube is coated with a layer of a lubricious polymer; wherein a layer of a lubricious polymer is positioned between an inside surface of the first tube and an outside surface of the second tube; further comprising a tissue collection receptacle connected to a proximal end of the second tube; wherein the distal end of the second tube is open and includes a distal facing cutting blade along a perimeter of the open tube end, wherein the distal facing cutting blade is moved relative to the treatment window of the first tube to cut a sample from material disposed within the aperture; wherein a side surface at the distal end of the second tube defines an aperture forming a cutting blade configured to cut a tissue sample upon rotation of the second tube within the first tube when tissue is positioned within the apertures defined by the first and second tubes;

Another embodiment of the invention is directed to a method of collecting a tissue sample in a body. The method includes providing a medical device comprising a first tube defining a lumen and an aperture at a distal end of the first tube and a second tube extending within the lumen of the first tube. The second tube defines a lumen and slots, at least some of the slots having sharp edges. The method includes inserting the medical device into a body; positioning a distal end of the first tube at a sample collection site such that the aperture receives tissue to be collected; and moving the second tube relative to the first tube such that the sharp edges of the slots cut multiple samples from the tissue disposed within the aperture.

In various embodiments, the method may include one or more of the following additional features: wherein moving the second tube relative to the first tube comprises reciprocating the second tube axially relative to the first tube; wherein moving the second tube relative to the first tube comprises rotating the second tube relative to the first tube; further comprising collecting the samples at a proximal end of the second tube by providing suction within the lumen of the second tube; wherein the aperture is defined by a side surface of the first tube; wherein the first tube defines multiple apertures along a side surface of the first tube; wherein the sharp edges are arranged to cut the plurality of samples substantially simultaneously; wherein the slots extend transverse to a longitudinal axis of the second tube; wherein at least a portion of slots extend in a spiral pattern along the second tube; wherein the first tube defines slots along a portion thereof; repositioning the distal end of the first tube at an additional sample collection site without removing the medical device from the body, such that the aperture receives tissue to be collected and moving the second tube relative to the first tube such that the sharp edges of the slots cut multiple samples from the tissue disposed within the aperture at the additional sample collection site; wherein the sharp edges cut the samples substantially simultaneously; wherein a distal end of the second tube is open and includes a distal facing cutting edge and the method further comprises positioning the distal facing cutting edge proximal of the aperture, positioning the aperture to receive tissue to be collected, and moving the second tube distally relative to the first tube such that the distal facing cutting edge shears the tissue received within the aperture.

In another embodiment, the medical device includes a first tube defining a lumen and an aperture at a distal end of the first tube. A second tube extends within the lumen of the first tube, and the second tube defines a lumen, slots arranged to provide flexibility to the second tube, and a cutting edge configured to shear tissue. The second tube is movable relative to the first tube such that the cutting edge cuts a sample from tissue disposed within the aperture.

In various embodiments, the medical device may include one or more of the following additional features: wherein at least some of the slots have sharp edges configured to shear tissue and wherein the second tube is movable relative to the first tube such that the sharp edges of the slots cut a plurality of biopsy samples from tissue disposed within the aperture; a drive connected to the second tube configured to provide movement of the second tube relative to the first tube; wherein the aperture is defined by a side surface of the first tube; wherein the first tube defines multiple apertures along a side surface of the first tube; wherein the sharp edges are arranged to cut the plurality of samples substantially simultaneously; wherein the slots extend transverse to a longitudinal axis of the second tube; wherein the slots extend only partially through a wall forming the second tube; wherein a proximal end of the second tube is connected to a vacuum source that provides suction within the lumen of the second tube; wherein the distal end of the second tube is open and the cutting edge is disposed along a perimeter of the open tube end, wherein the cutting edge is moved relative to the aperture of the first tube to cut a sample from tissue disposed within the aperture; wherein a side surface at a distal end of the second tube defines an aperture forming the cutting edge, the cutting edge configured to cut a tissue sample upon rotation of the second tube within the first tube when tissue is positioned within the apertures defined by the first and second tubes.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 7 is a cross-sectional view of a distal portion of a further alternative flexible biopsy device, according to an embodiment of the invention.

FIG. 8A is a cross-sectional view of the flexible biopsy device of FIG. 7 along line 8-8 of FIG. 7 prior to the collection of a biopsy specimen.

FIG. 8B is a cross-sectional view of the flexible biopsy device of FIG. 7 along line 8-8 of FIG. 7 after the collection of a biopsy specimen.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1:
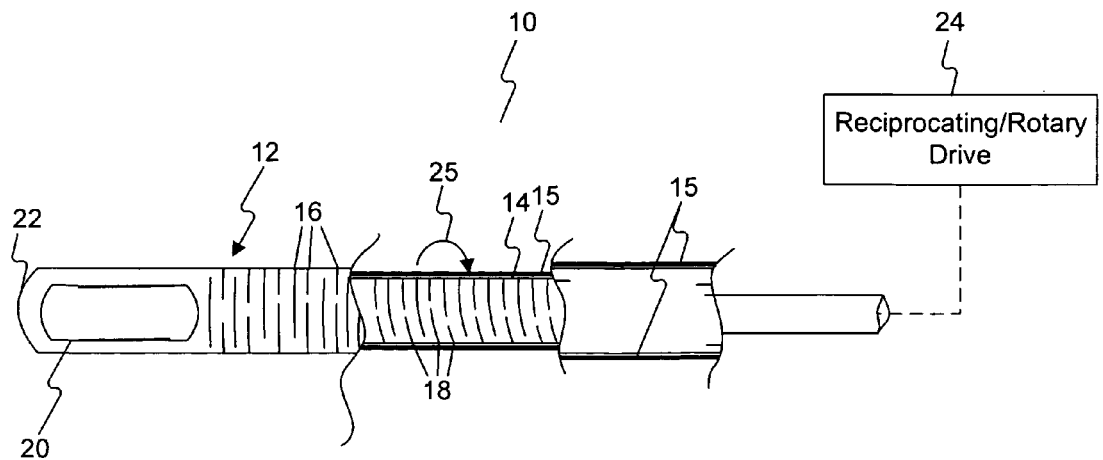
FIG. 1 is a top view of a flexible biopsy device according to an embodiment of the invention.

Referring to FIG. 1, one embodiment of a flexible biopsy device 10, according to the invention, includes an outer flexible tube 12 housing an inner flexible tube 14. As will be described in more detail below, the exterior of inner and outer flexible tubes 14 and 12 may be coated to include a polymer layer, such as, for example, layer 15. The outer flexible tube 12 includes slots 16, formed along a portion of the tube's length and having a particular pattern. Similarly, inner flexible tube 14 includes slots 18, also formed along a portion of the tube's length and having a particular pattern. A distal end (i.e. the end further from the biopsy device operator during use) of the outer flexible tube 12 includes a treatment window portion 20 that exposes a distal portion of the inner flexible tube 14. Treatment window 20 is an aperture defined by a side surface of tube 12. A plurality of apertures similar to window 20, having various shapes and sizes, may be defined at multiple positions along the side surface of tube 12 as desired, depending on the particular application and tissue sample sought. The distal end of the flexible biopsy device may include a rounded atraumatic tip 22 configured to avoid any unnecessary trauma to tissue during internal positioning of the device within a patient. Alternatively, the distal end of the flexible biopsy device may include a sharp tip configured to penetrate into tissue and position the treatment window 20 to a predetermined depth at a desired treatment site.

The proximal end (i.e. the end closer to the biopsy device operator during use) of the inner flexible tube 14 is configured for connection to a reciprocating and/or rotary drive device 24. Upon activation of the drive 24, inner flexible tube 14 is rotated, as depicted by arrow 25, about its longitudinal axis within the outer flexible tube 12. Alternatively or additionally, drive 24 may function to move the inner flexible tube 14 back and forth axially relative to tube 12, such that a distal portion of the inner flexible tube 14 shifts within the outer flexible tube 12 repeatedly across the treatment window portion 20.

The slots 16 and 18 formed along the outer flexible tube 12 and inner flexible tube 14 are provided along a predetermined portion of length of each tube and, as will be described more in detail below, assist in providing lateral flexibility while maintaining torsional stiffness in both tubes. In addition, a number of the slots 18 provided along a distal portion of the inner tube 14 may be formed to have sharp cutting edges that serve to shear samples of tissue disposed within the treatment window 20 upon actuation of the drive 24.

Figure 2:
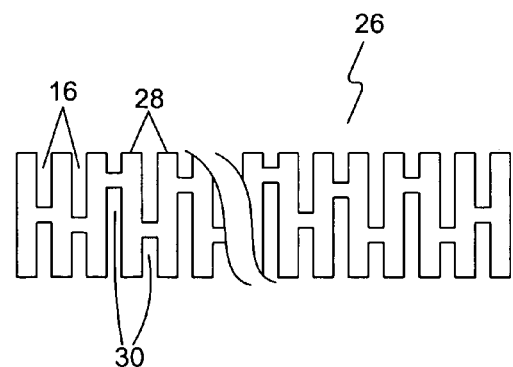
FIG. 2 is a fragmentary side view of a portion of a flexible tube segment illustrating a slotting pattern according to an embodiment of the invention.

Referring to FIG. 2, a portion of a flexible tube segment 26 is illustrated depicting a particular slotting pattern that can be used in the flexible biopsy device, according to embodiments of the present invention. The tube segment 26 depicted in FIG. 2 can be formed, for example, by a selective grinding process where a thin wall piece of hypo-tubing is modified through a cutting process to selectively form a particular cut or slot pattern. The particular pattern can be optimized to result in a tube having a particular desired flexibility and torsional stiffness. The slotting pattern can be formed according to the machining process described in U.S. Pat. No. 6,428,489, which is hereby incorporated by reference in its entirety. Other machining processes are possible, such as chemical etching, EDM (Electrical Discharge Machining), or laser cutting.

The cuts or slots 16 are specifically configured to form transverse beams 28 and axial beams 30 within the body of the tube segment 26. This configuration allows the slots 16 and beams 28, 30 to interact to provide for lateral flexibility in the hollow tube segment 26, while maintaining torsional stiffness. By controlling and varying the spacing, depth, and type of cuts, the flexure profile and torsional stiffness of the resulting tube may be selectively and relatively independently modified. Generally, the more closely spaced the slots 16 and the greater their depth, the more flexible will be the tube segment 26. However, modification of the exact shape, orientation, and spacing of the cuts will also allow selective modification or preservation of the torsional characteristics of the cross section independent of flexibility.

Figure 2A:
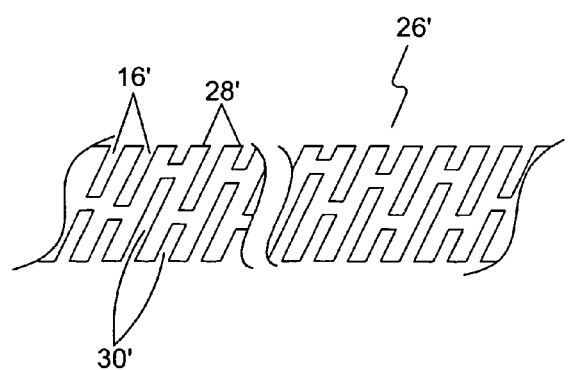
FIG. 2A is a fragmentary side view of a portion of a flexible tube segment illustrating a spiral slotting pattern according to an embodiment of the invention.

Exemplary dimensions for the slots 16 include, but are not limited to, slot widths of between about 0.008 inches and 0.020 inches, and slots formed with depths of up to about 80% of the tube diameter. FIGS. 1 and 2 illustrate the slots 16 and 18 as being formed perpendicular to the longitudinal axis of the tube along which they are formed. In an alternative configuration illustrated in FIG. 2A, slots 16' may be formed in a spiral pattern along a portion of the tube. As described above with regard to FIG. 2, the spiral cuts or slots 16' are similarly configured to form transverse beams 28' and axial beams 30' within the body of the tube segment 26'. The spiral slots 16' can be formed with a predetermined pitch along a portion of the tube or the pitch may also be varied along the length of the tube in order to allow selective modification or preservation of both the torsional characteristics and flexibility for the tube. For example, it may be desirable to impart greater flexibility to the distal portion of the tube for accessing tortuous pathways of a patient's internal body lumens. The particular pattern used in the flexible biopsy device may include a combination of spiral slots 16' and perpendicular slots 16.

In addition to the dual benefits of lateral flexibility and torsional stiffness, the slotting pattern of tube segment 26 can also be formed to provide sharp cutting edges particularly suited to shear biopsy tissue samples like a razor blade. The width of the slots will determine the volume level of the samples acquired. Accordingly, the design of the slots 16 along a distal portion of the inner flexible tube 14 will determine the size of the acquired sample and the potential length of any acquired samples. The inner and outer tubes 14 and 12 may be formed of any material suitable for the machining process described above. Exemplary materials include, but are not limited to, stainless steel and metallic alloys of nickel/titanium (commonly referred to as nitinol). The materials are not limited to metals. Stiff polymer materials such as polyimide or other additional stiff cast polymers that can be made flexible by means of the above process, for example, are usable.

Figure 3:
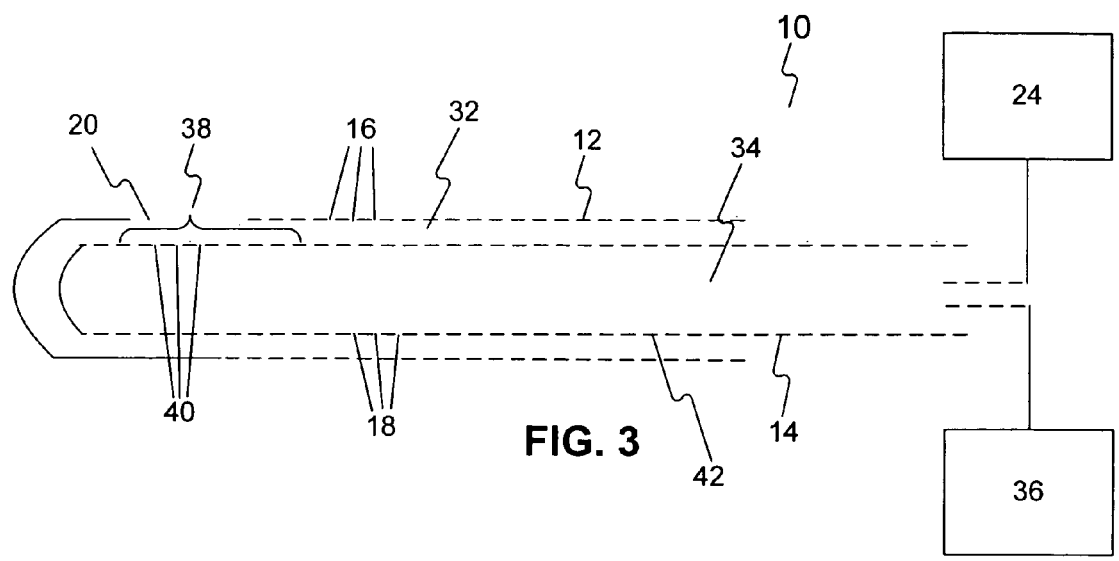
FIG. 3 is a cross-sectional view of a distal portion of a flexible biopsy device according to an embodiment of the invention.

FIG. 3 depicts a cross-sectional view of a distal portion of a flexible biopsy device 10. As illustrated, inner flexible tube 14 is housed within a lumen 32 of outer flexible tube 12. In at least one embodiment of the flexible biopsy device, the outer flexible tube has an outer diameter capable of being positioned within a working channel having an inside diameter of approximately 0.048 inches. Inner flexible tube 14 includes an inner lumen 34 that may be connected at its proximal end to a vacuum source 36 and a specimen container (not shown) for retrieving collected biopsy tissue samples. Alternatively, inner lumen 34 can itself serve as the specimen collection receptacle. The vacuum source and specimen container may be integral with or separate from drive 24, and may be any suitable source and container known in the art.

Inner tube 14 includes slots 18, formed along at least a portion of the tube's length. Outer flexible tube 12 includes slots 16, also formed along at least a portion of the tube's length. While FIG. 3 denotes the pattern of slots 16 and 18 generally as a dashed line, it is to be understood that the slotting pattern can be selectively altered as noted above with regard to the parameters of the spacing, depth, orientation, and type of cuts along both tubes 12 and 14.

As noted above, at least a distal portion 38 of the inner flexible tube 14 includes a number of slots formed to have sharp cutting edges 40 configured to shear samples of tissue disposed within the treatment window 20 upon actuation of the drive 24. These slots are spaced so as to permit the simultaneous taking of a plurality of tissue samples without removal of the device from the body. Accordingly, the slot pattern along the distal portion 38 of inner flexible tube 14 is also selectively altered with regard to the parameter of slot shape as well as edge sharpness, depending on the desired biopsy specimen size.

A portion of the inside surface of inner flexible tube 14 may be coated with a thin layer 42 of a lubricious polymer material, such as for example, polytetrafluoroethylene (PTFE). Examples of other suitable lubricious polymer materials include, but are not limited to, parylene, and hydrophilic polymer materials. An inside layer of polymer material, such as the layer 42 illustrated in FIG. 3, aids in the capturing of biopsy samples within the inner lumen 34 by proving a low friction surface against which any captured specimen potentially contacts during a specimen capturing procedure. The lower friction surface reduces the potential for any specimen to become lodged or caught against the inside surface of inner tube 14, particularly when the inner tube material is formed of a relatively higher friction material, such as, for example, stainless steel.

An additional thin layer of a lubricious polymer material may be coated along one of the surfaces between inner flexible tube 14 and outer flexible tube 12 (i.e. either the outer surface of inner flexible tube 14 or the inner surface of outer flexible tube 12). Such a coating can help prevent galling of the facing tube surfaces during movement of tube 14 relative to tube 12 during activation of drive 24.

Figure 4:
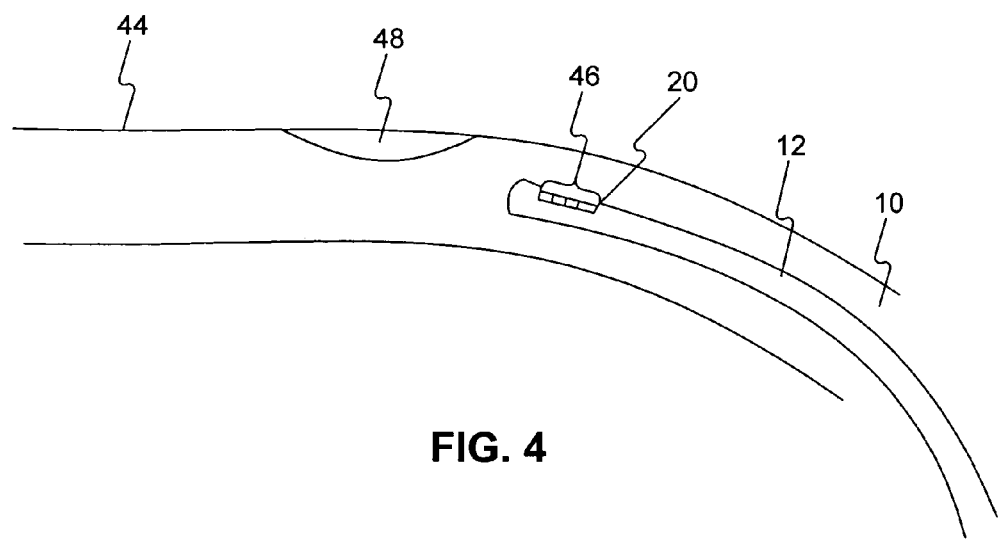
FIG. 4 depicts the positioning of the flexible biopsy device of FIG. 1 within an anatomical lumen of a patient.

Referring to FIG. 4, flexible biopsy device 10 may be positioned at an internal treatment site, for example, such as within a patient's anatomical lumen 44. The positioning may be performed by any suitable method known in the art, and may include known imaging and viewing techniques. For example, the positioning may be attained by extending device 10 through a channel of an endoscope. As described above, the flexible biopsy device 10 is configured to be flexible enough to extend through the tortuous pathways of a patient's anatomical lumens in order to reach a desired treatment site. In order to facilitate accurate positioning of the device 10, the outer flexible lumen 12 may include a deflection control mechanism, such as, for example, deflection control wires configured to laterally deflect the device 10 to reach a particular anatomical lumen pathway. As seen in FIG. 4, the treatment window portion 20, and an exposed portion 46 of the inner flexible tube 14, can be positioned to retrieve biopsy samples, such as, for example, tissue samples from lesion 48 within patient lumen 44. As noted above, the distal end of the flexible biopsy device may include a sharpened tip configured for penetrating tissue. In such a configuration the treatment window portion 20 can be positioned to retrieve biopsy samples at a particular penetration depth at a target tissue site.

Figure 5:
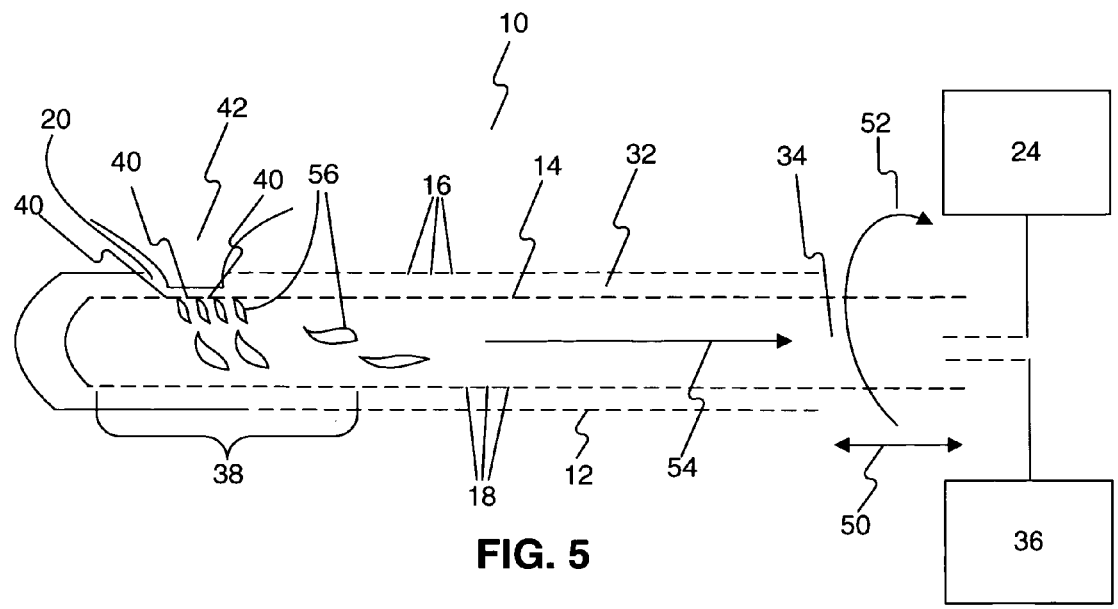
FIG. 5 is a cross-sectional view of a distal portion of the flexible biopsy device of FIG. 1 during the collection of a biopsy specimen.

FIG. 5 illustrates a cross-sectional view of a distal portion of the flexible biopsy device 10, during the collection of one or more biopsy specimens. After the treatment window portion 20 is properly positioned near the tissue to be sampled, such as the lesion 42, the operator can activate the vacuum source 36. Activating vacuum source 36 will pull a portion of the targeted tissue within the treatment window 20 and near an exposed portion (see item 46 of FIG. 4) of the inner flexible tube 14 along a distal portion 38 of the inner flexible tube 14.

As noted above, the distal portion 38 of inner flexible lumen 14 includes a number of slots 18 formed to have sharp cutting edges 40. These slots are selectively altered with regard to the parameter of slot shape as well as edge sharpness depending on the desired biopsy specimen size. When the lesion 42 is drawn near the sharp cutting edges 40 upon the application of suction by way of vacuum source 36, the operator will activate the drive 24 in order to move the inner flexible tube 14 relative to outer flexible tube 12. Arrow 50 represents the back and forth movement of inner tube 14 when drive 24 is configured to impart reciprocating motion to inner tube 14. Alternatively or in addition to such axial movement, arrow 52 represents rotational movement of inner tube 14 about its own longitudinal axis when drive 24 is configured to impart rotary motion to inner tube 14. Irrespective of whether drive 24 imparts reciprocating or rotational movement to inner tube 14, the combination of suction (represented by arrow 54) acting on the target tissue and the movement of slot cutting edges 40 against the target tissue results in the shearing of tissue samples 56 to be drawn within inner lumen 34.

As seen in FIG. 5, the slot cutting edges 40 along the distal portion 38 of the inner flexible tube 14 act to sever tissue samples 56 of the lesion 42. The hollow lumen 34 of inner flexible tubular member allows for the collection of multiple biopsy tissue samples 56 without having to remove the device from the anatomical lumen after each specimen is collected. In addition, the size and shape of the slots along the distal portion 38 of the inner flexible tube 14 can be selected to correspond to the desired specimen size. Accordingly, the flexible biopsy device 10 provides for both multiple tissue samples as well as potentially larger tissue samples as compared to other biopsy devices of similar outer diameter, such as pinch type biopsy devices.

In addition to the lumen 34 of inner flexible tube 14, suction may also be applied to lumen 32 of outer flexible tube 12. Providing suction within lumen 32 provides the added benefits of more reliably pulling the target tissue within treatment window 20 prior to shearing any tissue samples, as well as capturing any samples that pass between the inner surface of outer tube 12 and the inner surface of inner tube 14. Such suction prevents clogging and maintains space between the moving parts of the flexible biopsy device. When suction is applied to the lumens 32, 34 of both tubes 12, 14, the proximal end of both tubes can lead to the same receptacle for specimen retrieval. Alternatively, the lumens themselves can function as the receptacle or a separate container can be attached to the proximal end of the flexible biopsy device.

As seen in FIG. 5, the proximal end of device 10 may include a reciprocating and/or rotary drive device 24. Drive 24 may be any suitable handle or actuation mechanism known in the medical arts for providing relative axial and/or rotary motion between tubes 12 and 14. Such mechanisms may include, for example, spool/thumb ring arrangements, scissors-like handles, or other known devices. As further examples, the reciprocating movement may be achieved through the use of a motor device or through the actuation of a loaded trigger device using a spring mechanism actuated by the biopsy device operator. In addition, the drive 24 may be configured, for example, through the use of an indexing cam, to impart combined reciprocating and rotational motion to the inner flexible tube 14. This combined motion would allow the slot cutting edges 40 to simultaneously move in both axial and rotational directions in order to more effectively shear tissue samples like the movement of a knife.

Figure 6:
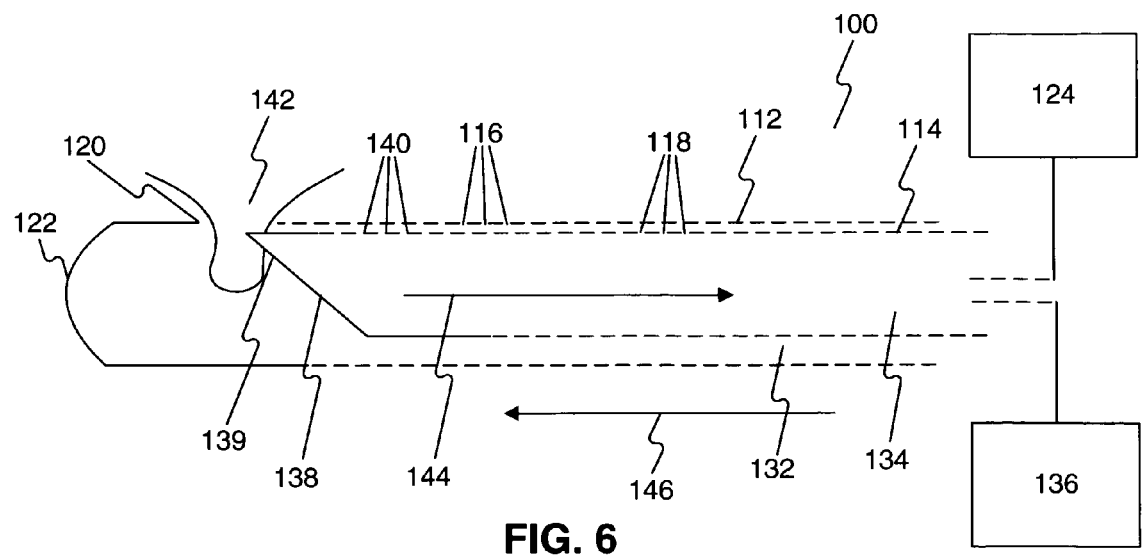
FIG. 6 is a cross-sectional view of a distal portion of an alternative flexible biopsy device, according to an embodiment of the invention.

FIG. 6 illustrates a cross-sectional view of a distal portion of an alternative flexible biopsy device 100, according to an embodiment of the invention. Flexible biopsy device 100 is similar is most respects to previously described flexible biopsy device 10. Device 100 includes an outer flexible tube 112 having a lumen 132 housing an inner flexible tube 114. The outer flexible tube 112 includes slots 116, formed along at least a portion of the tube's length and having a particular pattern. Similarly, inner flexible tube 114 may include slots 118, also formed along at least a portion of the tube's length and having a particular pattern. The distal end of the outer flexible tube 112 includes a treatment window portion 120 that exposes a distal portion of the inner flexible tube 114. The distal end of the flexible biopsy device 100 may include a rounded atruamatic tip 122 configured to avoid any unnecessary trauma to tissue during internal positioning of the device within a patient.

Just as in the device of FIG. 1, the proximal end of the inner flexible tube 114 is configured for connection to a reciprocating and/or rotary drive device 124. Upon activation of the drive 124, inner flexible tube 114 can be rotated or moved back and forth such that a distal portion of the inner flexible tube 114, having a number of slots 118 formed to have sharp cutting edges 140, shifts within the outer flexible tube 112 repeatedly across the treatment window portion 120. As illustrated, inner flexible tube 114 includes an inner lumen 134 that may be connected at its proximal end to a vacuum source 136 and a specimen container for retrieving collected biopsy tissue samples.

The distal end of inner flexible tube 114 includes the additional feature of an open distal end including a forward cutting blade 138 along the distal facing open tube perimeter. The forward cutting blade 138 may include a beveled cutting surface 139 to assist in shearing a tissue sample, such as a portion of lesion 142. The forward cutting blade 138 can be used to obtain a large tissue sample upon forward movement of the cutting blade 138 across the treatment window portion 120 when a target tissue sample is positioned within the outer flexible tube 112 through the use of suction represented by arrow 144. The forward movement of blade 138, represented by arrow 146, can be effected by a single forward stroke of the distal portion of inner flexible tube 114 across the treatment window portion 120 through actuation of the drive 124. Alternatively, the forward cutting movement can be actuated through a spring loaded drive mechanism at the proximal end of the device, or any other suitable method of activation.

The embodiment of FIG. 6 can alternate between the shearing of tissue samples through the use of cutting edges 140, in the manner of described in connection with FIG. 1 above, and the shearing of a single large tissue sample through the use of forward cutting blade 138. The difference in cutting modes will depend upon the initial starting position of inner flexible tube 114 within outer flexible tube 112. For example, in order to shear a single large tissue sample, the forward cutting blade 138 will need to be positioned proximal of the window treatment portion 120. Conversely, in order to cut tissue samples with the use of cutting edges 140, the inner flexible tube 114 will need to be positioned such that treatment window 120 directly exposes target tissue to the cutting edges 140 of the inner tube 114.

FIG. 7 illustrates a cross-sectional view of a distal portion of an alternative flexible biopsy device 200, according to an embodiment of the invention. Flexible biopsy device 200 is similar is most respects to previously described flexible biopsy device 10. Device 200 includes an outer flexible tube 212 having a lumen 232 housing an inner flexible tube 214. Just as in the previously described embodiments, both outer flexible tube 212 and inner flexible tube 214 include slots 216 and 218 respectively, formed along a portion of each tube's length and having a particular pattern. The distal end of the outer flexible tube 212 includes a treatment window portion 220 that exposes a distal portion of the inner flexible tube 214.

Just as in the device of FIG. 1, the proximal end of the inner flexible tube 214 is configured for connection to a reciprocating/rotary drive device 224. Upon activation of the drive 224, inner flexible tube 214 can be rotated or moved back and forth such that a distal portion of the inner flexible tube 214, having a number of slots 218 formed to have sharp cutting edges 240, shifts within the outer flexible tube 212 repeatedly across the treatment window portion 220. As illustrated, inner flexible tube 214 includes an inner lumen 234 that may be connected at its proximal end to a vacuum source 236 and a specimen container for retrieving collected biopsy tissue samples.

The distal end of inner flexible tube 214 includes the additional feature of a laterally facing open treatment window 221 defining a cutting blade 225 along the perimeter of the window 221 formed along an outside surface of tube 214 at the tube's distal end. The perimeter of window 221 is configured to cut a large tissue sample upon rotation of the inner flexible tube 214 within the outer flexible tube 212 when a target tissue sample is pulled within the treatment window 220 and within the perimeter of window 221 through the use of suction from vacuum source 236. FIG. 8A illustrates a cross-sectional view of the flexible biopsy device 200 along line 8-8 of FIG. 7. As seen in FIG. 8A, the target tissue, polyp 242 along anatomical lumen 245, is positioned within both the treatment window 220 and treatment window 221, thereby extending into lumen 234 of inner flexible tube 214.

FIG. 8B illustrates the rotation of the inner flexible tube 214 within the outer flexible tube 212. The cutting blade 225 (FIG. 7) and the shearing force generated from the interaction of the perimeter of treatment window 220 against the perimeter of treatment window 221, act to sever the polyp 242. Next, suction from vacuum source 236 pulls polyp 242 through lumen 234 of inner flexible tube 214 for collection in a specimen container.

Just as in the embodiment of FIG. 6, the flexible biopsy device 200 can alternate between two tissue collection modes. Flexible biopsy device 200 can shear tissue samples by means of reciprocating motion through the use of cutting edges 240, in the manner of described in connection with FIG. 1 above. Alternatively, the flexible biopsy device 200 can shear a single large tissue sample upon rotation of treatment window 221 formed along an outside surface of tube 214 at the tube's distal end.

The flexible biopsy device according to embodiments of the present invention may also be configured so as to conduct electrosurgical energy to the patient's tissues in order to cauterize the treated tissue region during and/or after sample collection. Accordingly, the inner flexible 14 tube may be connected to a source of high frequency current so as to conduct electrosurgical energy to target tissue in the region of the treatment window 20. The energy may be provided in monopolar or bipolar form at a distal portion (such as, for example, portion 38 of the inner flexible tube 14 of FIGS. 3 and 5).

In a monopolar mode, only one of either inner tube 14 of outer tube 12 would be connected to a source of electrosurgical energy and an electric circuit would be completed with an external return electrode pad attached at some point along a patient's external skin surface. Alternatively, in a bipolar mode, electrosurgical energy may be provided at a distal portion of the flexible biopsy device such that one of tubes 12,14 acts as an active electrode with the other tube acting as the return electrode in a bipolar circuit through tissue. In such an embodiment, the active and return electrodes would necessarily be insulated from each other in order to prevent a short circuit condition. If conductive, the flexible biopsy device may be electrically connected to a suitable power source known in the art (e.g., RF generator) via suitable electrical connections known in the art (e.g., electrical leads and/or wires).

It is to be understood that any feature described with reference to a particular figure or embodiment may be repeated in and utilized in any of the other embodiments or figures disclosed in this application. For example, it is intended that any embodiment may include the use of polymer coatings on both inside and outside surfaces of the inner and outer flexible tubes or the use of electrosurgical energy in order to aid in tissue sample collection and cauterization. As another example, in all embodiments, the slotting pattern may be formed along a large portion of both the inner tube and the outer tube or, in the alternative, only along a small portion as necessary with regard to the particular application and the device parameters desired, such as, for example, flexibility, torsional stiffness, and biopsy specimen size.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a first tube defining a lumen and an aperture at a distal end of the first tube, the aperture facing a first side of the first tube, the first tube further defining a plurality of discrete slots proximal the aperture and facing a second side of the first tube opposite the first side, wherein each of the discrete slots includes a passageway extending completely through the second side of the first tube, wherein a distal tip of the first tube covers an entirety of a distal-most portion of the lumen of the first tube; and
   a second tube extending within the lumen of the first tube, the second tube defining a lumen and slots, at least some of the slots of the second tube having sharp edges configured to shear tissue, wherein adjacent slots of the second tube are longitudinally spaced from each other along a longitudinal axis of the second tube;
   wherein the second tube is configured for lateral deflection, and wherein the second tube is movable relative to the first tube such that the sharp edges cut a plurality of samples from tissue disposed within the aperture.

2. The medical device of claim 1, further comprising a drive connected to the second tube configured to provide movement of the second tube relative to the first tube.

3. The medical device of claim 2, wherein the drive moves the second tube relative to the first tube with rotary movement.

4. The medical device of claim 1, wherein the second tube moves axially relative to the first tube.

5. The medical device of claim 4, wherein axial movement of the second tube relative to the first tube causes the sharp edges of the slots of the second tube to cut the plurality of samples from tissue.

6. The medical device of claim 1, wherein the aperture is defined by a side surface of the first tube.

7. The medical device of claim 1, wherein the first tube defines multiple apertures along a side surface of the first tube.

8. The medical device of claim 1, wherein the slots of the second tube extend transverse to the longitudinal axis of the second tube.

9. The medical device of claim 1, wherein the slots of the second tube extend only partially through a wall forming the second tube.

10. The medical device of claim 1, wherein at least a portion of slots of the second tube extend in a spiral pattern along the second tube.

11. The medical device of claim 1, wherein at least one of the first and second tube is electronically conductive and configured to act as an electrode for conducting current to tissue.

12. The medical device of claim 1, wherein a proximal end of the second tube is connected to a vacuum source that provides suction within the lumen of the second tube.

13. The medical device of claim 1, further comprising a tissue collection receptacle connected to a proximal end of the second tube.

14. The medical device of claim 1, wherein a distal end of the second tube is open and includes a distal facing cutting blade along a perimeter of the open distal end, wherein the distal facing cutting blade is moved relative to the aperture of the first tube to cut a sample from material disposed within the aperture.

15. The medical device of claim 1, wherein a side surface at the distal end of the second tube defines an aperture forming a cutting blade configured to cut a tissue sample upon rotation of the second tube within the first tube when tissue is positioned within the apertures defined by the first and second tubes.

16. The medical device of claim 1, further comprising a deflection control wire configured for laterally deflecting the first and second tubes.

17. The medical device of claim 1, wherein the slots of the second tube form a pattern of transverse beams and axial beams.

18. The medical device of claim 1, wherein the slots of the second tube are arranged along opposite sides of the second tube.

19. The medical device of claim 1, wherein the plurality of discrete slots of the first tube includes slots arranged along opposite sides of the first tube.

20. The medical device of claim 1, wherein the plurality of discrete slots of the first tube are arranged transverse a longitudinal axis of the first tube and include axially adjacent slots and radially adjacent slots, the axially adjacent slots defining transverse beams, and the radially adjacent slots defining axial beams.

21. The medical device of claim 1, wherein the distal tip includes a sharp tip configured to penetrate tissue.

22. A method of collecting a tissue sample in a body, comprising:
   inserting a medical device into the body, the medical device comprising:
      a first tube defining a lumen and an aperture at a distal end of the first tube, the aperture facing a first side of the first tube, the first tube further defining a plurality of discrete slots proximal the aperture and facing a second side of the first tube opposite the first side, wherein each of the discrete slots includes a passageway extending completely through the second side of the first tube, wherein a distal tip of the first tube covers an entirety of a distalmost portion of the lumen of the first tube; and a second tube extending within the lumen of the first tube, the second tube defining a lumen and slots, at least some of the slots of the second tube having sharp edges, wherein adjacent slots of the second tube are longitudinally spaced from each other along a longitudinal axis of the second tube;

inserting the medical device into the body such that the medical device is laterally deflected during insertion;

positioning a distal end of the first tube at a sample collection site such that the aperture receives tissue to be collected; and moving the second tube relative to the first tube such that the sharp edges of the slots of the second tube cut multiple samples from the tissue disposed within the aperture.

23. The method of claim 22, wherein moving the second tube relative to the first tube comprises reciprocating the second tube axially relative to the first tube.

24. The method of claim 22, wherein moving the second tube relative to the first tube comprises rotating the second tube relative to the first tube.

25. The method of claim 22, further comprising collecting the samples at a proximal end of the second tube.

26. The method of claim 22, further comprising providing suction within the lumen of the second tube.

27. The method of claim 22, wherein the aperture is defined by a side surface of the first tube.

28. The method of claim 22, wherein the first tube defines multiple apertures along a side surface of the first tube.

29. The method of claim 22, wherein the slots of the second tube extend transverse to the longitudinal axis of the second tube.

30. The method of claim 22, wherein the slots of the second tube extend only partially through a wall forming the second tube.

31. The method of claim 22, wherein at least a portion of slots of the second tube extend in a spiral pattern along the second tube.

32. The method of claim 22, further comprising:
repositioning the distal end of the first tube at an additional sample collection site without removing the medical device from the body, such that the aperture receives tissue to be collected; and
moving the second tube relative to the first tube such that the sharp edges of the slots cut multiple samples from the tissue disposed within the aperture at the additional sample collection site.

33. The method of claim 22, wherein a distal end of the second tube is open and includes a distal facing cutting edge; the method further comprising:
positioning the distal facing cutting edge proximal of the aperture;
positioning the aperture to receive tissue to be collected; and
moving the second tube distally relative to the first tube such that the distal facing cutting edge shears the tissue received within the aperture.

34. The method of claim 22, wherein moving the second tube relative to the first tube comprises both reciprocating the second tube axially relative to the first tube and rotating the second tube relative to the first tube.

35. The method of claim 22, wherein positioning the distal end of the first tube at a sample collection site comprises laterally deflecting the first and second tubes with a deflection control wire.

36. The method of claim 22, wherein the slots of the second tube form a pattern of transverse beams and axial beams.

37. The method of claim 22, wherein the slots of the second tube are arranged along opposite sides of the second tube.

38. The method of claim 22, wherein the plurality of discrete slots of the first tube includes slots arranged along opposite sides of the first tube.

39. The method of claim 22, wherein axial movement of the second tube relative to the first tube causes the sharp edges of the slots of the second tube to cut the multiple samples from tissue.

40. The method of claim 22, wherein the plurality of discrete slots of the first tube include are arranged transverse a longitudinal axis of the first tube and include axially adjacent slots and radially adjacent slots, the axially adjacent slots defining transverse beams, and the radially adjacent slots defining axial beams.

41. The medical of claim 22, wherein the distal tip includes a sharp tip configured to penetrate tissue.

42. A medical device comprising:
a first tube defining a lumen and an aperture at a distal end of the first tube, the aperture facing a first side of the first tube, the first tube further defining a plurality of discrete slots proximal the aperture and facing a second side of the first tube opposite the first side, wherein each of the discrete slots includes a passageway extending completely through the second side of the first tube, wherein a distal tip of the first tube covers an entirety of a distalmost portion of the lumen of the first tube; and
a second tube extending within the lumen of the first tube, the second tube defining a lumen, slots arranged to provide flexibility to the second tube such that the second tube is configured for lateral deflection, wherein adjacent slots of the second tube are longitudinally spaced from each other along a longitudinal axis of the second tube, and a cutting edge configured to shear tissue;
wherein the second tube is movable relative to the first tube such that the cutting edge cuts a sample from tissue disposed within the aperture.

43. The medical device of claim 42, wherein at least some of the slots of the second tube have sharp edges configured to shear tissue.

44. The medical device of claim 42, further comprising a drive connected to the second tube configured to provide movement of the second tube relative to the first tube.

45. The medical device of claim 44, wherein the drive moves the second tube relative to the first tube with rotary movement.

46. The medical device of claim 44, wherein the drive moves the second tube axially relative to the first tube.

47. The medical device of claim 44, wherein the drive moves the second tube relative to the first tube with combined rotary and axial movement.

48. The medical device of claim 42, wherein the aperture is defined by a side surface of the first tube.

49. The medical device of claim 42, wherein the first tube defines multiple apertures along a side surface of the first tube.

50. The medical device of claim 42, wherein the slots of the second tube extend transverse to the longitudinal axis of the second tube.

51. The medical device of claim 42, wherein the slots of the second tube extend only partially through a wall forming the second tube.

52. The medical device of claim 42, wherein a proximal end of the second tube is connected to a vacuum source that provides suction within the lumen of the second tube.

53. The medical device of claim 42, wherein the distal end of the second tube is open and the cutting edge is disposed along a perimeter of the open tube end, wherein the cutting edge is moved relative to the aperture of the first tube to cut a sample from tissue disposed within the aperture.

54. The medical device of claim 42, wherein a side surface at a distal end of the second tube defines an aperture forming the cutting edge, the cutting edge configured to cut a tissue sample upon rotation of the second tube within the first tube when tissue is positioned within the apertures defined by the first and second tubes.

55. The medical device of claim 42, further comprising a deflection control wire configured for laterally deflecting the first and second tubes.

56. The medical device of claim 42, wherein the slots of the second tube form a pattern of transverse beams and axial beams.

57. The medical device of claim 42, wherein the slots of the second tube are arranged along opposite sides of the second tube.

58. The medical device of claim 42, wherein the plurality of discrete slots of the first tube includes slots arranged along opposite sides of the first tube.

59. The medical device of claim 42, wherein axial movement of the second tube relative to the first tube causes the cutting edge to cut the sample from tissue.

60. The medical device of claim 42, wherein the plurality discrete slots of the first tube are arranged transverse a longitudinal axis of the first tube and include axially adjacent slots and radially adjacent slots, the axially adjacent slots defining transverse beams, and the radially adjacent slots defining axial beams.

61. The medical device of claim 42, wherein the distal tip includes a sharp tip configured to penetrate tissue.

62. A medical device, comprising:
a first tube defining a lumen and an aperture at a distal end of the first tube, wherein a distal tip of the first tube covers an entirety of a distalmost portion of the lumen of the first tube; and
a second tube extending within the lumen of the first tube, the second tube defining a lumen and slots, at least some of the slots having sharp edges configured to shear tissue;
wherein the second tube is configured for lateral deflection, and wherein the second tube is axially movable relative to the first tube such that the axial movement causes the sharp edges to cut a plurality of samples from tissue disposed within the aperture, wherein at least a portion of slots of the second tube extend in a spiral pattern along the second tube.

63. The medical device of claim 62, wherein a distal end of the second tube is open and includes a distal facing cutting blade along a perimeter of the open distal end, wherein the distal facing cutting blade is moved relative to the aperture of the first tube to cut a sample from material disposed within the aperture.

64. The medical device of claim 62, wherein a side surface at the distal end of the second tube defines an aperture forming a cutting blade configured to cut a tissue sample upon rotation of the second tube within the first tube when tissue is positioned within the apertures defined by the first and second tubes.

65. The medical device of claim 62, wherein the aperture faces a first side of the first tube, the first tube further defining a plurality of discrete slots proximal the aperture and facing a second side of the first tube opposite the first side.

66. The medical device of claim 62, wherein the distal tip includes a sharp tip configured to penetrate tissue.

67. A method of collecting a tissue sample in a body, comprising:
inserting a medical device into the body such that the medical device is laterally deflected during insertion, the medical device comprising:
a first tube defining a lumen and an aperture at a distal end of the first tube, wherein a distal tip of the first tube covers an entirety of a distalmost portion of the lumen of the first tube; and
a second tube extending within the lumen of the first tube, the second tube defining a lumen and slots, at least some of the slots having sharp edges;
positioning a distal end of the first tube at a sample collection site such that the aperture receives tissue to be collected;
axially moving the second tube relative to the first tube such that the axial movement causes the sharp edges of the slots to cut multiple samples from the tissue disposed within the aperture; and
rotating the second tube relative to the first tube.

68. The method of claim 67, wherein at least a portion of slots of the second tube extend in a spiral pattern along the second tube.

69. The method of claim 67, wherein a distal end of the second tube is open and includes a distal facing cutting edge; the method further comprising:
positioning the distal facing cutting edge proximal of the aperture;
positioning the aperture to receive tissue to be collected; and
moving the second tube distally relative to the first tube such that the distal facing cutting edge shears the tissue received within the aperture.

70. The medical device of claim 67, wherein the aperture faces a first side of the first tube, the first tube further defining a plurality of discrete slots proximal the aperture and facing a second side of the first tube opposite the first side.

71. The medical device of claim 67, the aperture faces a first side of the first tube, the first tube further defining a plurality of discrete slots proximal the aperture and facing a second side of the first tube opposite the first side.

72. The medical of claim 67, wherein the distal tip includes a sharp tip configured to penetrate tissue.

73. A medical device, comprising:
a first tube defining a lumen and an aperture at a distal end of the first tube, wherein a distal tip of the first tube covers an entirety of a distalmost portion of the lumen of the first tube; and
a second tube extending within the lumen of the first tube, the second tube defining a lumen, slots arranged to provide flexibility to the second tube such that the second tube is configured for lateral deflection, and a cutting edge configured to shear tissue;
wherein the second tube is axially movable relative to the first tube such that the axial movement causes the cutting edge to cut a sample from tissue disposed within the aperture.

74. The medical device of claim 73, wherein a distal end of the second tube is open and the cutting edge is disposed along a perimeter of the open distal end, wherein the cutting edge is moved relative to the aperture of the first tube to cut a sample from tissue disposed within the aperture.

75. The medical device of claim 73, wherein a side surface at a distal end of the second tube defines an aperture forming the cutting edge, the cutting edge configured to cut a tissue sample upon rotation of the second tube within the first tube when tissue is positioned within the apertures defined by the first and second tubes.

76. The medical device of claim 73, wherein the distal tip includes a sharp tip configured to penetrate tissue.

\* \* \* \* \*